(12) United States Patent
Uemori et al.

(10) Patent No.: US 11,388,323 B2
(45) Date of Patent: Jul. 12, 2022

(54) IMAGING APPARATUS AND IMAGING METHOD

(71) Applicant: SONY CORPORATION, Tokyo (JP)

(72) Inventors: Takeshi Uemori, Tokyo (JP); Atsushi Ito, Kanagawa (JP); Shinichiro Gomi, Tokyo (JP); Yusuke Moriuchi, Kanagawa (JP); Kenichiro Nakamura, Saitama (JP)

(73) Assignee: SONY CORPORATION, Tokyo (JP)

( * ) Notice: Subject to any disclaimer, the term of this patent is extended or adjusted under 35 U.S.C. 154(b) by 50 days.

(21) Appl. No.: 16/964,191

(22) PCT Filed: Jan. 22, 2019

(86) PCT No.: PCT/JP2019/001762
§ 371 (c)(1),
(2) Date: Jul. 22, 2020

(87) PCT Pub. No.: WO2019/151029
PCT Pub. Date: Aug. 8, 2019

(65) Prior Publication Data
US 2021/0037173 A1 Feb. 4, 2021

(30) Foreign Application Priority Data
Feb. 5, 2018 (JP) .............................. JP2018-017956

(51) Int. Cl.
*A61B 1/06* (2006.01)
*H04N 5/225* (2006.01)
(Continued)

(52) U.S. Cl.
CPC ............. *H04N 5/2256* (2013.01); *G06N 3/08* (2013.01); *G06V 10/143* (2022.01); *H04N 5/243* (2013.01); *H04N 9/07* (2013.01)

(58) Field of Classification Search
CPC ........ H04N 5/2256; H04N 5/243; H04N 9/07; H04N 5/23218; H04N 5/23219;
(Continued)

(56) References Cited

U.S. PATENT DOCUMENTS 8,233,037 B2 * 7/2012 Matsui ................... A61B 1/042
345/506
8,269,824 B2 * 9/2012 Hasegawa .......... A61B 1/00009
348/45
(Continued)

FOREIGN PATENT DOCUMENTS

| CN | 1077635452 A | 1/2018 |
| JP | 2003-093336 A | 4/2003 |

(Continued)

OTHER PUBLICATIONS

International Search Report and Written Opinion of PCT Application No. PCT/JP2019/001762, dated Apr. 16, 2019, 09 pages of ISRWO.

*Primary Examiner* — Howard D Brown, Jr.
(74) *Attorney, Agent, or Firm* — Chip Law Group

(57) ABSTRACT

Provided are an imaging apparatus and an imaging method that make it possible to apply light having an optimum wavelength to capture an image without a user taking heed of a type of an imaging object. A wavelength of light optimum for analysis of a target is specified as an effective wavelength from a multispectral image of the target on which white light is applied, and light of the effective wavelength is applied upon the target. The target in this state is captured as a multispectral image, and the target is analyzed on a basis of a spectral image of an effective wavelength.

15 Claims, 11 Drawing Sheets

(51) Int. Cl.
*G06N 3/08* (2006.01)
*H04N 5/243* (2006.01)
*H04N 9/07* (2006.01)
*G06V 10/143* (2022.01)

(58) Field of Classification Search
CPC .. H04N 5/2354; H04N 5/332; H04N 9/04559; G06K 9/2018; G06K 9/6217; G06K 2009/4657; G06K 2209/05; G06N 3/08; G06N 3/0454; G06T 1/0007; A61B 1/00; A61B 1/045; G01N 21/27; G02B 23/24
See application file for complete search history.

(56) References Cited

U.S. PATENT DOCUMENTS

| | | | | |
|---|---|---|---|---|
| 8,633,977 | B2* | 1/2014 | Higuchi | A61B 5/0084 |
| | | | | 348/70 |
| 10,045,431 | B2* | 8/2018 | Otani | H05B 41/38 |
| 10,321,816 | B2* | 6/2019 | Morimoto | A61B 1/07 |
| 10,368,728 | B2* | 8/2019 | Ito | A61B 1/00045 |
| 10,869,590 | B2* | 12/2020 | Yamamoto | A61B 1/00006 |
| 2008/0086028 | A1* | 4/2008 | Matsui | A61B 1/041 |
| | | | | 348/45 |
| 2018/0084980 | A1* | 3/2018 | Watanabe | A61B 1/0638 |

FOREIGN PATENT DOCUMENTS

| | | |
|---|---|---|
| JP | 2005-348902 A | 12/2005 |
| JP | 2006-288612 A | 10/2006 |
| JP | 2012-120764 A | 6/2012 |
| JP | 2012-152333 A | 8/2012 |
| JP | 2014-154982 A | 8/2014 |
| WO | 2016/194150 A1 | 12/2016 |

\* cited by examiner

IMAGING APPARATUS AND IMAGING METHOD

CROSS REFERENCE TO RELATED APPLICATIONS

This application is a U.S. National Phase of International Patent Application No. PCT/JP2019/001762 filed on Jan. 22, 2019, which claims priority benefit of Japanese Patent Application No. JP 2018-017956 filed in the Japan Patent Office on Feb. 5, 2018. Each of the above-referenced applications is hereby incorporated herein by reference in its entirety.

TECHNICAL FIELD

The present disclosure relates to an imaging apparatus and an imaging method as well as a program and particularly to an imaging apparatus and an imaging method as well as a program in which light having an optimum wavelength can be applied to capture an image without the user taking heed of the type of an imaging object.

BACKGROUND ART

Disclosed is a method in which an edge component is extracted from an endoscopic image, the complexity of the edge component is detected, it is then determined on the basis of the complexity whether the imaging object is imaged by close-up imaging or distant view imaging, and then, a matrix parameter for generating a spectral image from an RGB (Red Green Blue) image is switched to generate spectral images having wavelengths different from each other between close-up imaging and distant view imaging (refer to PTL 1).

CITATION LIST

Patent Literature

[PTL 1]
Japanese Patent Laid-Open No. 2014-154982

SUMMARY

Technical Problem

However, in the method of PTL 1, a combination of wavelengths of a spectral image to be generated is prepared in advance and flexible coping according to various situations of an imaging target is not implemented.

Further, it is difficult to generate a spectral image having a freely-selected wavelength with high accuracy from an RGB image, and an applicable scene is limited.

The present disclosure has been made in view of such a situation as described above and makes it possible to apply light having an optimum wavelength to capture an image without the user taking heed of the type of an imaging object.

Solution to Problem

The imaging apparatus according to one aspect of the present disclosure is an imaging apparatus including a white light source unit configured to apply white light on a target, an imaging unit configured to capture a multispectral image of the target, a target identification unit configured to specify a wavelength of light optimum for analysis of the target as an effective wavelength from the multispectral image of the target on which the white light is applied, and a variable wavelength light source unit configured to apply light having the effective wavelength on the target.

The imaging method according to one aspect of the present disclosure is an imaging method including a white light source process for applying white light on a target, an imaging process for capturing a multispectral image of the target, a target identification process for specifying a wavelength of light optimum for analysis of the target as an effective wavelength from the multispectral image of the target on which the white light is applied, and a variable wavelength light application process for applying light having the effective wavelength on the target.

The program according to one aspect of the present disclosure is a program for causing a computer to function as a white light source unit that applies white light on a target, an imaging unit that captures a multispectral image of the target, a target identification unit that specifies a wavelength of light optimum for analysis of the target as an effective wavelength from the multispectral image of the target on which the white light is applied, and a variable wavelength light source unit that applies light having the effective wavelength on the target.

In one aspect of the present disclosure, white light is applied on a target and a multispectral image of the target is captured. Then, a wavelength of light optimum for analysis of the target is specified as an effective wavelength from the multispectral image of the target on which the white light is applied, and light having the effective wavelength is applied on the target.

Advantageous Effect of Invention

With one aspect of the present disclosure, light having an optimum wavelength can be applied to capture an image without the user taking heed of the type of a subject.

DESCRIPTION OF EMBODIMENTS

In the following, suitable embodiments of the present disclosure are described in detail with reference to the accompanying drawings. It is to be noted that, in the present specification and the drawings, components having the same functional configurations are denoted by identical reference signs, and overlapping description of them is omitted.

Further, the description is given in the following order.
1. First Embodiment
2. Second Embodiment
3. Example of Execution by Software

1. First Embodiment

Figure 1:
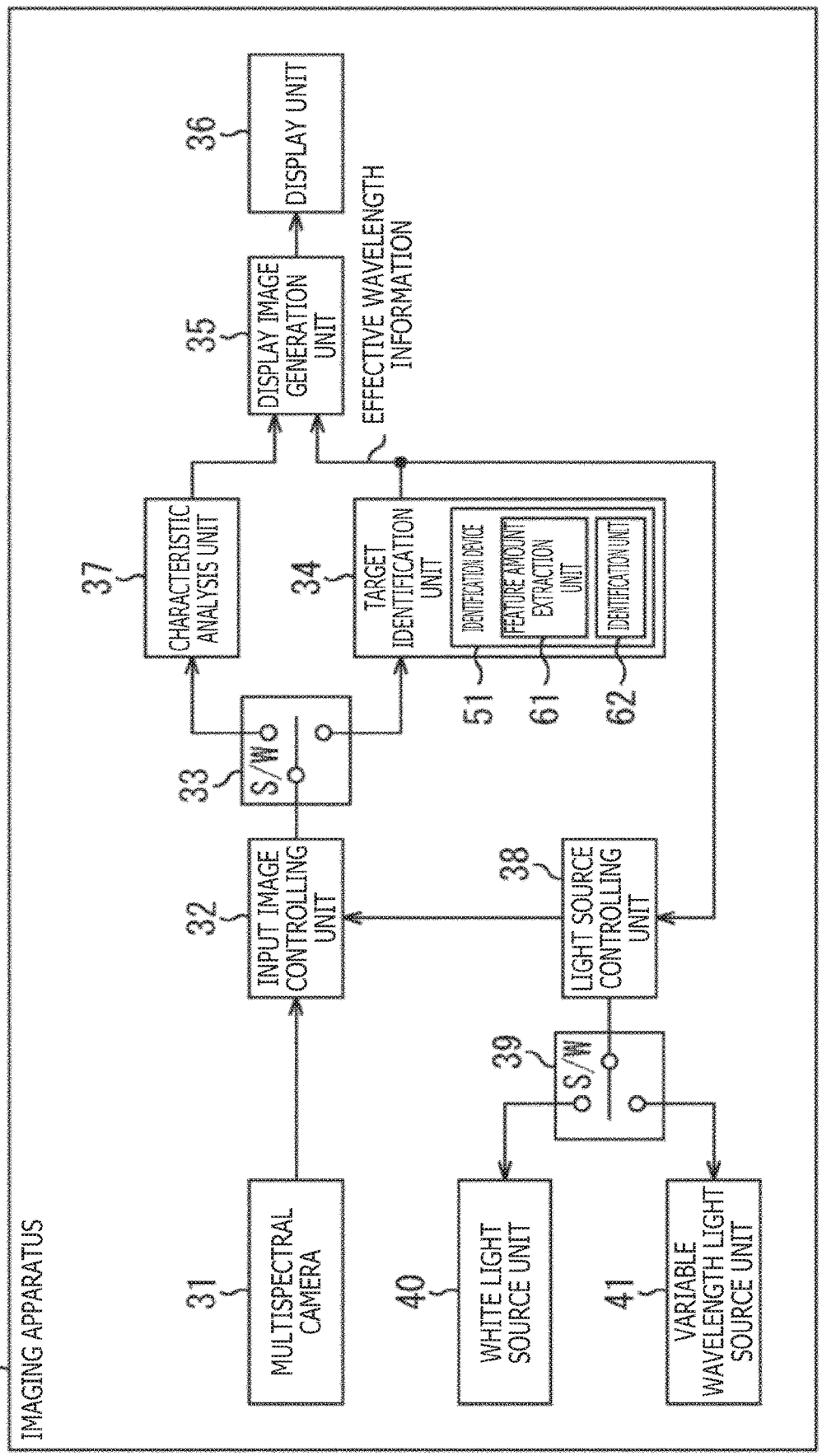
FIG. 1 is a view depicting an example of a configuration of a first embodiment of an imaging apparatus according to the present disclosure.

FIG. 1 depicts an example of a configuration of a first embodiment of an imaging apparatus according to the present disclosure.

An imaging apparatus 11 of FIG. 1 principally captures a visceral tissue or an affected lesion of a human body as a multispectral image by using an endoscopic device, analyzes the visceral tissue or the affected lesion on the basis of the captured multispectral image, and then displays a result of the analysis.

It is to be noted that, in the description of the present embodiment, the description is given assuming that the imaging apparatus 11 of FIG. 1 captures a visceral tissue or an affected lesions of a human body as a multispectral image and analyzes the visceral tissue or the affected lesion on the basis of the captured multispectral image. However, a similar configuration may be applied to any other use. For example, the imaging apparatus 11 of FIG. 1 may capture a vegetable or a fruit as a multispectral image and analyze the sugar content, salt, or the degree of ripeness from the captured multispectral image.

More particularly, the imaging apparatus 11 first captures an image under white light by multispectral imaging and identifies a site, a lesion or the like of an organ that is an imaging object from the captured image by using an identification device configured using a neural network such as a CNN (Convolutional Neural Network).

Further, the imaging apparatus 11 specifies a wavelength, which is optimum for identification, of light to be applied upon an imaging object, on the basis of a parameter that is obtained upon identification.

Then, the imaging apparatus 11 causes a variable wavelength light source unit to emit light of the specified optimum wavelength and apply the light upon the imaging object to acquire a spectral image (spectral image) of the optimum wavelength that is higher in wavelength dissolution than that under white light.

Consequently, it becomes possible for the imaging apparatus 11 to identify the imaging object that is a target in detail and analyze a characteristic of the identifyed imaging object with high accuracy. Further, it becomes possible for the imaging apparatus 11 to display a characteristic of a visceral tissue or a lesion in an easy-to-understand manner by generating a pseudo color image from a spectral image captured under white light and a spectral image captured under narrow band light having a wavelength optimum for identification or analysis of the imaging object and generating an image that emphasizes a characteristic or a result of analysis of the visceral tissue or the lesion that is an imaging object.

In the following, a detailed configuration of the imaging apparatus 11 of FIG. 1 is described.

The imaging apparatus 11 includes a multispectral camera 31, an input image controlling unit 32, a switch (S/W) 33, a target identification unit 34, a display image generation unit 35, a display unit 36, a characteristic analysis unit 37, a light source controlling unit 38, another switch (S/W) 39, a white light source unit 40, and a variable wavelength light source unit 41.

The multispectral camera 31 captures and outputs a multispectral image (a spectral image of a plurality of bands (wavelength bands)) including a plurality of wide-band spectral images to the input image controlling unit 32.

In the case where white light is applied from the white light source unit 40 upon an imaging object that is a target and a multispectral image captured by the multispectral camera 31 is supplied, the input image controlling unit 32 controls the switch 33 to establish connection to the target identification unit 34 and outputs the multispectral image to the target identification unit 34.

Further, in the case where a multispectral image captured by the multispectral camera 31 is supplied while, on the basis of effective wavelength information hereinafter described, light of an effective wavelength supplied from the light source controlling unit 38 is applied upon an imaging object that is a target from the variable wavelength light source unit 41, the input image controlling unit 32 controls the switch 33 to output a spectral image corresponding to the effective wavelength information from within the multispectral image to the characteristic analysis unit 37.

In the case where the switch 33 is connected to the target identification unit 34 under the control of the input image controlling unit 32, the multispectral image outputted from the input image controlling unit 32 is outputted, but in the case where the switch 33 is connected to the characteristic analysis unit 37, a spectral image of a wavelength band corresponding to the effective wavelength information is outputted.

The target identification unit 34 uses an identification device 51, in which relations between targets and multispectral images that are captured in a state in which white light is applied upon the imaging object by the white light source unit 40 are learned in advance, to identify a target that becomes an imaging object, on the basis of a multispectral image.

Further, the target identification unit 34 outputs information regarding a wavelength of light that is effective for identification and is to be applied upon the imaging object, on the basis of a parameter in the inside of the identification device 51 obtained upon identification, as effective wavelength information, to the display image generation unit 35 and the light source controlling unit 38.

The characteristic analysis unit 37 identifies an imaging object that is a target, on the basis of a spectral image of an effective wavelength from within a multispectral image captured by the multispectral camera 31, in a state in which light of the wavelength effective for imaging an imaging object is applied by the variable wavelength light source unit 41. Further, the characteristic analysis unit 37 analyzes a characteristic of the target on the basis of a result of the identification and outputs a result of the analysis to the display image generation unit 35.

It is to be noted that the characteristic analysis unit 37 may, for example, include an identification device including a neural network such as a CNN (corresponding to the identification device 51 in the target identification unit 34) and so forth and may thereby classify a degree of progress of a site and a lesion. Such an identification device as just described can be implemented by learning spectral images (spectral images) of different degrees of progress of various sites and lesions in advance. Further, as another example, a shape and so forth of a blood vessel or an organizational structure in a spectral image (spectral image) of narrow-band light may be analyzed such that it is made possible to determine whether or not it is a lesion.

Here, in the case of an endoscopic device that is the present embodiment, the target is a living tissue of various sites of the human body. Therefore, the image that is eventually required in the present disclosure is an image on which it is possible to observe capillaries of a mucosal surface, slight thickening of a mucous membrane, a deep blood vessel and so forth in order to determine whether the tissue is a normal tissue or a lesion tissue.

For example, in the case of a gastrointestinal tumor, it is important to observe a collection of capillaries or a pattern of the same, and in order to facilitate observation of them, for example, a narrow band light spectral image (Narrow Band Imaging (NBI)) that is captured by applying light of a narrow wavelength band whose wavelength is 415 nm or 540 nm is required.

Generally, the wavelength band of a narrow band light spectral image that is useful for diagnosis differs depending upon the site and the lesion that become the target of analysis.

Therefore, for example, fluorescence observation in which blue light of a narrow wavelength band is applied and the intensities of self-fluorescence at a normal tissue and a lesion tissue are emphatically displayed depending upon a difference in color between them, infrared observation in which infrared light is used and a blood vessel at a deep location of a mucous membrane or blood flow information is emphatically displayed and like observation are also used depending upon the site or the lesion of a diagnosis target.

After the target identification unit 34 identifies a site and a lesion tissue of an imaging object that becomes the target described above, on the basis of a multispectral image, the target identification unit 34 generates and outputs effective wavelength information, which is information regarding a wavelength of light optimum for imaging of a spectral image necessitated for observation of the identified target to the light source controlling unit 38.

It is to be noted that, for example, a CNN (Convolution Neural Network) is used for the identification device 51 provided in the target identification unit 34, and, for particulars of the identification device 51 in which a CNN is used, "Grad-CAM: Visual Explanations from Deep Networks via Gradient-based Localization" (http://arxiv.org/pdf/1610.02391.pdf) is to be referred to.

By using a CNN, the identification device 51 can analyze to which spectral image of a wavelength attention is paid and can determine a wavelength effective for identification of the target.

More particularly, the identification device 51 that uses a CNN includes a feature amount extraction unit 61 including a plurality of convolution layers and a pooling layer and an identification unit 62 that classifies a result of the identification of the target into a corresponding class on the basis of feature amounts from the feature amount extraction unit 61. The last layer of the identification unit 62 converts a feature amount of each class into a probability score using a soft-max function and applies the probability score as a tag to the class. The target identification unit 34 outputs an identification result of the class that indicates the highest probability score.

Further, the number of effective wavelengths to be outputted is any number equal to or smaller than the number of bands of the multispectral camera 31 and is decided in the order of the magnitude of the degree of attention among spectral images obtained by a technique using a CNN.

The light source controlling unit 38 controls the switch 39 to change the white light source unit 40 or the variable wavelength light source unit 41 such that white light or light of a wavelength based on the effective wavelength information is emitted and applied upon the target that becomes an imaging object.

More particularly, the light source controlling unit 38 controls, in a first process, the white light source unit 40 to emit white light. Then, in a next process, the light source controlling unit 38 controls the variable wavelength light source unit 41 to emit, on the basis of the decided effective wavelength information, light of a corresponding wavelength.

By such an operation as described above, the multispectral camera 31 captures, in the first process, a multispectral image of a state in which white light from the white light source unit 40 is applied upon the target that is an imaging object. The target is identifyed from the multispectral image and an effective wavelength optimum for measurement of the target as an identification result is specified and outputted as effective wavelength information.

Then, by the next process, the multispectral camera 31 captures a multispectral image of a state in which light of a narrow band wavelength corresponding to the effective wavelength information is applied from the variable wavelength light source unit 41 on the target that becomes an imaging object. A spectral image corresponding to the effective wavelength information within the multispectral image captured at this time is used by the characteristic analysis unit 37 to analyze the target that is an imaging object.

The display image generation unit 35 superimposes the multispectral image captured in a state in which white light is emitted and an analysis result of a characteristic of the target that is an imaging object, to generate an image. Then, the display image generation unit 35 outputs the image to the display unit 36 including an organic EL (Electro Luminescence) display, an LCD (Liquid Crystal Display) or the like such that it is displayed on the display unit 36.

More particularly, the display image generation unit 35 generates a pseudo color image by using a multispectral image captured in a state in which white light is applied and a spectral image of an effective wavelength corresponding to the effective wavelength information in a state in which light of the effective wavelength is applied. The pseudo color image is displayed on the display unit 36. It is to be noted that generation of a pseudo color image is described in detail below with reference to FIGS. 4 and 5.

<Sensitivity Characteristic of Multispectral Camera and Narrow Band Distribution of Light Emitted by Variable Length Light Source Unit>

Now, a relationship between a sensitivity characteristic of the multispectral camera 31 and a narrow band distribution of light emitted from the variable wavelength light source unit 41 is described with reference to FIGS. 2 and 3.

Figure 2:
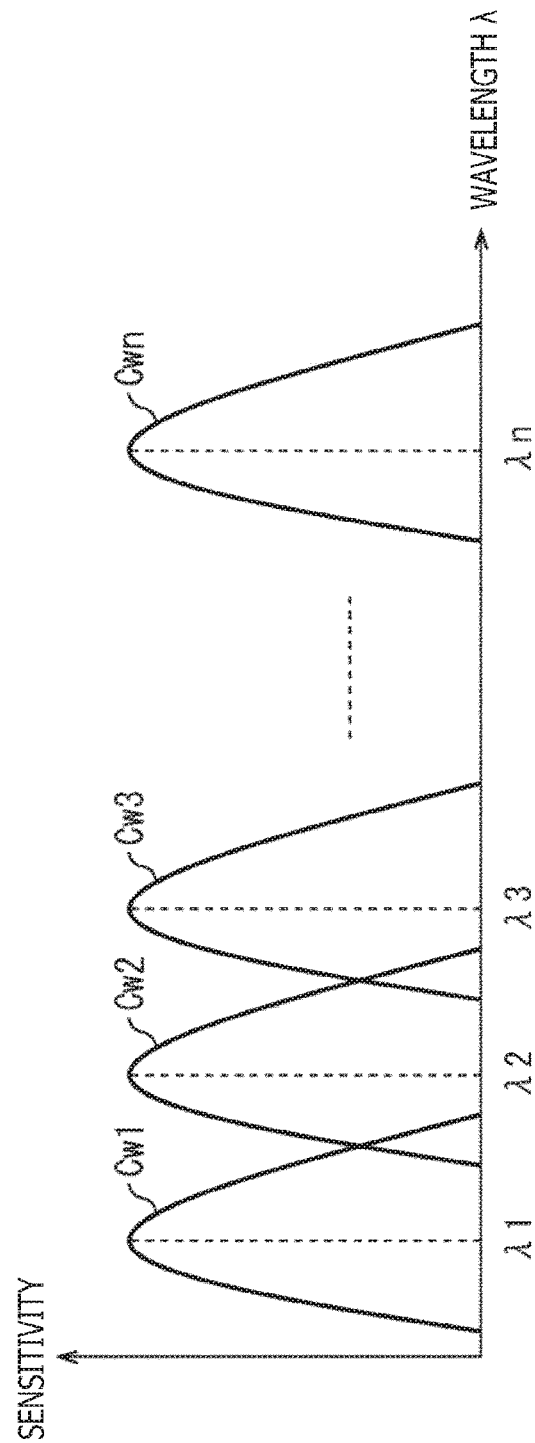
FIG. 2 is a view illustrating a sensitivity characteristic of a multispectral camera.

The multispectral camera 31 captures such a multispectral image as depicted, for example, in FIG. 2, which includes a spectral image of a band Cw1 having a peak at a wavelength $\lambda 1$, a spectral image of a band Cw2 having a peak at a wavelength $\lambda 2$, a spectral image of a band Cw3 having a peak at a wavelength $\lambda 3$, . . . , and a spectral image of a band Cwn having a peak at a wavelength $\lambda n$.

It is to be noted that an example in which a multispectral image including wide-band spectral images of n different bands is captured is depicted here. As depicted in FIG. 2, the band of each spectral image is a wide band, and the bands overlap in wavelength partially on boundaries thereof.

In particular, as depicted in FIG. 2, in an initial operation, white light of a wide wavelength band is applied from the white light source unit 40 upon a target that is an imaging object, and spectral images under white light are obtained by the multispectral camera 31. This makes it possible to acquire spectral reflectance information in all wavelength bands of the target and acquire a multispectral image that is desirable in identifying which cite and lesion the target are.

Figure 3:
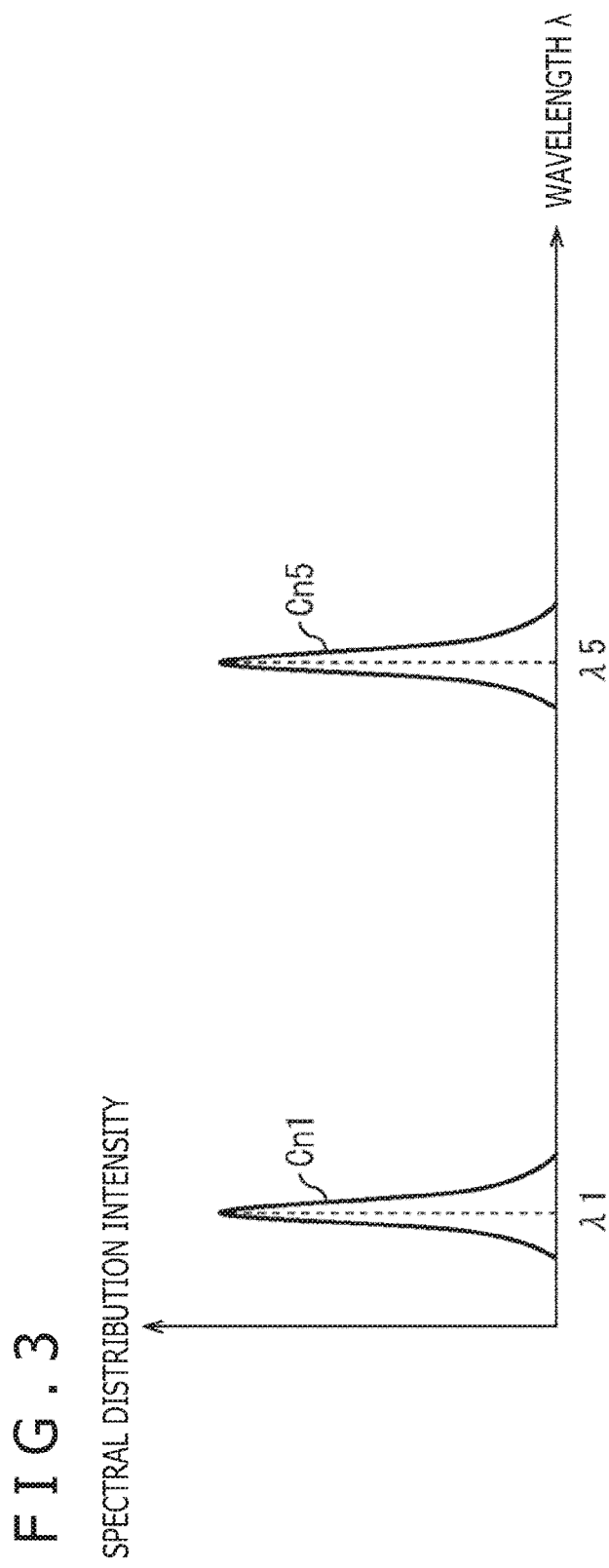
FIG. 3 is a view illustrating a narrow-band spectral intensity characteristic of light emitted by a variable wavelength light source unit.

On the other hand, the variable wavelength light source unit 41 emits, as light of a band that is a narrow band optimum for identification of the target that is an imaging object, for example, light of a spectral distribution including light of the band Cn1 having a peak at the wavelength $\lambda 1$ and light of the band Cn5 having a peak at the wavelength $\lambda 5$, as depicted in FIG. 3.

In particular, the variable wavelength light source unit 41 emits light having a spectral distribution of a wavelength band that is one of the bands Cn1 to Cnn of narrow bands in comparison with frequency bands of the bands of the multispectral camera 31 and is optimum for imaging of the target that is an imaging object.

It is to be noted that FIG. 3 depicts an example in which light of a spectral distribution including a combination of the bands Cn1 and Cn5 having a peak at the wavelengths $\lambda 1$ and $\lambda 5$, and light of a spectral distribution of a combination of bands other than the above or more than the above or only of one of the bands may be emitted.

<Generation of Pseudo Color Image>

Now, generation of a pseudo color image by the display image generation unit 35 is described with reference to FIGS. 4 and 5.

The display image generation unit 35 generates a pseudo color image from spectral images (spectral images) of bands captured under white light and under narrow band light and including wavelength bands. Then, the display image generation unit 35 superimposes results of analysis by the characteristic analysis unit 37 to generate a display image and causes the display image to be displayed on the display unit 36.

For example, considered is a case in which the effective wavelengths $\lambda 1$ and $\lambda 5$ are obtained by the target identification unit 34 and light having a spectral characteristic including a combination of the bands Cn1 and Cn5 having a peak at the wavelengths $\lambda 1$ and $\lambda 5$ is emitted from the variable wavelength light source unit 41. Here, it is assumed that a multispectral image includes spectral images of the five bands Cn1 to Cn5 having a peak at the wavelengths $\lambda 1$ to $\lambda 5$, respectively.

Figure 4:
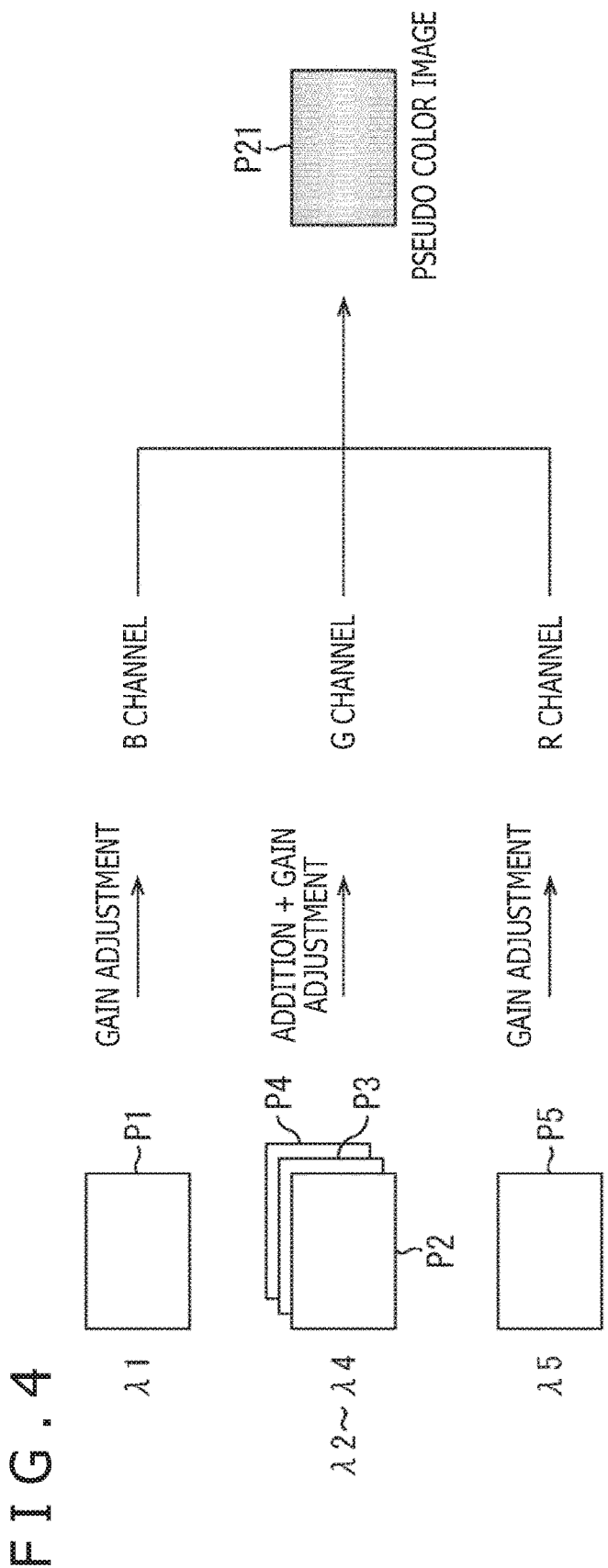
FIG. 4 is a view illustrating a generation method of a pseudo color image.

In this case, for example, as depicted in FIG. 4, the display image generation unit 35 adjusts the gain of spectral images P1 and P5 of the bands Cn1 and Cn5 having a peak at the effective wavelengths $\lambda 1$ and $\lambda 5$, respectively, and then allocates the spectral images P1 and P5 of the adjusted gains independently to a B channel and an R channel, respectively.

Then, the display image generation unit 35 adds spectral images P2 to P4 of the bands Cw2 to Cw4 having a peak at the wavelengths $\lambda 2$ to $\lambda 4$, respectively, which are intermediate wavelengths between the wavelengths $\lambda 1$ and $\lambda 5$, adjusts the gain of a resulting image, and allocates the image of the adjusted gain to a G channel.

In this manner, the display image generation unit 35 generates such a pseudo color image P21 as depicted in FIG. 4 by synthesizing the images allocated to the R, G, and B channels.

At this time, the spectral images P1 and P5 of the bands Cw1 and Cw5 having a peak at the wavelengths $\lambda 1$ and $\lambda 5$, respectively, may be spectral images captured under white light or may be spectral images captured in narrow band light. It is to be noted that to which ones of the R, G, and B channels the spectral images P1 and P5 and the image obtained by addition of the spectral images P2 to P4 are allocated may be any other than that described above.

Figure 5:
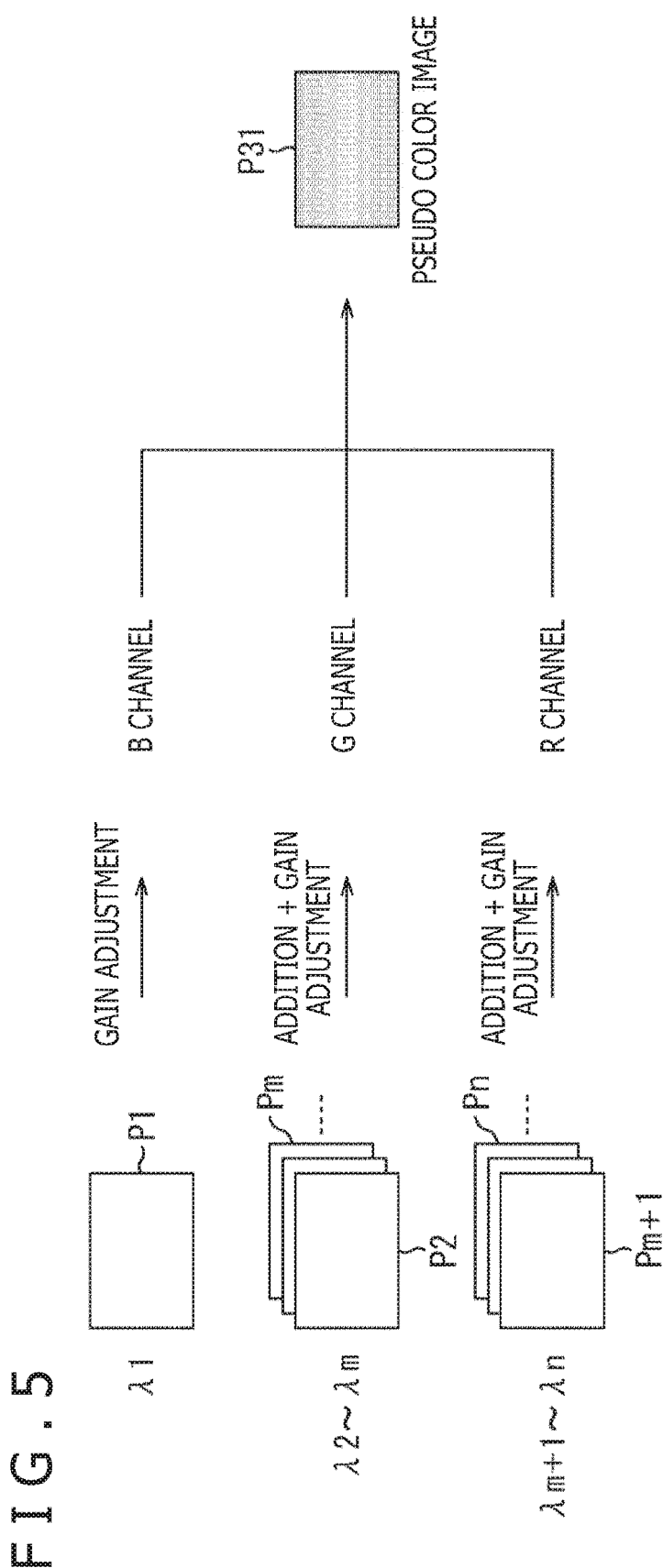
FIG. 5 is a view illustrating another generation method of a pseudo color image.

Further, in the case where, for example, only the wavelength $\lambda 1$ is the effective wavelength, the display image generation unit 35 allocates the spectral image P1 of the band Cw1 having a peak at the wavelength $\lambda 1$ that is the effective wavelength as depicted in FIG. 5 to one channel among the B, G, and R channels. In FIG. 5, the spectral image P1 of the band Cw1 having a peak at the wavelength $\lambda 1$ is allocated to the B channel.

Then, the display image generation unit 35 adds spectral images P2 to Pm of bands B2 to Bm having a peak at the wavelengths $\lambda 2$ to $\lambda m$, respectively, and adjusts the gain of a resulting image to allocate the image of the adjusted gain to one of the remaining two channels (in FIG. 5, to the G channel). Then, the display image generation unit 35 adds spectral images Pm+1 to Pn of the bands Cwm+1 to Cwn having a peak at the wavelengths $\lambda m+1$ to $\lambda n$, respectively, and adjusts the gain of a resulting image to allocate the image of the adjusted gain to the other channel of the remaining two channels (in FIG. 5, to the R channel).

The display image generation unit 35 generates such a pseudo color image P31 as depicted in FIG. 5 by synthesizing the images allocated to the R, G, and B channels in such manner.

<Imaging Process by Imaging Apparatus of FIG. 1>

Figure 6:
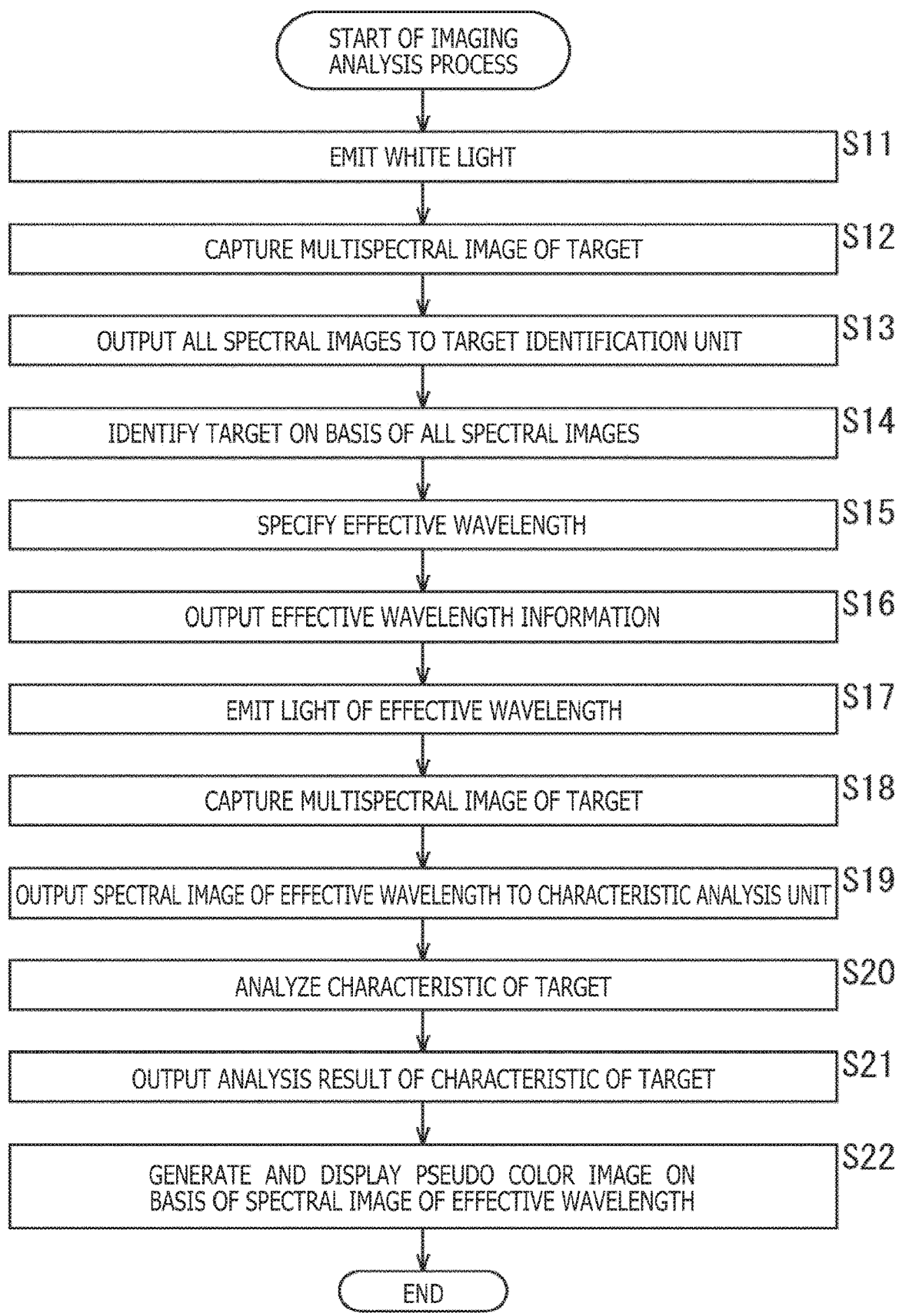
FIG. 6 is a flowchart illustrating an imaging process by the imaging apparatus of FIG. 1.

Now, an imaging process by the imaging apparatus 11 of FIG. 1 is described with reference to a flowchart of FIG. 6.

In step S11, the light source controlling unit 38 controls the switch 39 to establish connection to the white light source unit 40 and controls the white light source unit 40 to apply white light on a target that is an imaging object within an imaging range of the multispectral camera 31. At this time, the light source controlling unit 38 controls the white light source unit 40 to output information indicating that white light is being emitted, to the input image controlling unit 32.

In step S12, the multispectral camera 31 captures the target that is an imaging object as a multispectral image in the state in which white light is applied from the white light source unit 40 and outputs the multispectral image to the input image controlling unit 32.

In step S13, the input image controlling unit 32 controls the switch 33 to establish connection to the target identification unit 34 and outputs all spectral images of the multispectral image captured by the multispectral camera 31 to the target identification unit 34.

In step S14, the target identification unit 34 identifies the target by using the identification device 51 including a CNN or the like, on the basis of the multispectral image captured by the multispectral camera 31, that is, all of the spectral images.

In step S15, the target identification unit 34 specifies a wavelength of light effective for analysis of the target as an effective wavelength, on the basis of a parameter of the identification device 51 when the target is discriminated.

In step S16, the target identification unit 34 outputs information regarding the specified effective wavelength, as effective wavelength information, to the display image generation unit 35 and the light source controlling unit 38. At this time, the target identification unit 34 outputs the multispectral image to the display image generation unit 35 together with the effective wavelength information.

In step S17, the light source controlling unit 38 controls the switch 39 to establish connection to the variable wavelength light source unit 41 and causes the variable wavelength light source unit 41 to emit light of a wavelength based on the effective wavelength information so as to be applied upon the target that is an imaging object. At this time, the light source controlling unit 38 outputs the effective wavelength information to the input image controlling unit 32.

In step S18, the multispectral camera 31 captures the target that is an imaging object, as a multispectral image, in a state in which light of a wavelength based on the effective wavelength information is applied from the variable wavelength light source unit 41. Then, the multispectral camera 31 outputs the captured multispectral image to the input image controlling unit 32. At this time, the white light source unit 40 is placed into a state in which it does not emit white light.

In step S19, the input image controlling unit 32 controls the switch 33 to establish connection to the characteristic analysis unit 37 and outputs a spectral image corresponding to the effective wavelength information from within the multispectral image supplied from the multispectral camera 31, to the characteristic analysis unit 37.

In step S20, the characteristic analysis unit 37 identifies and analyzes the target that is an imaging object, on the basis of the spectral image, supplied thereto from the input image controlling unit 32, of a band corresponding to the effective wavelength information.

In step S21, the characteristic analysis unit 37 outputs a result of the analysis based on the identification result of the target that is an imaging object to the display image generation unit 35. At this time, the characteristic analysis unit 37 outputs the spectral image of the band corresponding to the effective wavelength information to the display image generation unit 35 together with the result of the analysis.

In step S22, the display image generation unit 35 generates a pseudo color image on the basis of the analysis result and the spectral image corresponding to the effective wavelength information from the characteristic analysis unit 37 as well as the effective wavelength information and the multispectral image from the target identification unit 34, superimposes the result of the analysis, and causes a resulting image to be displayed on the display unit 36. In regard to the generation method of the pseudo color image, the pseudo color image is generated, for example, by the method described hereinabove with reference to FIG. 4 or 5.

By the series of processes described above, a multispectral image in a state in which white light is applied upon a target that is an imaging object is captured, the target is recognized, the recognized target is observed to specify a wavelength of light optimum for analysis, and the wavelength is outputted as effective wavelength information. Then, in a state in which light of a wavelength corresponding to the effective wavelength information is applied on the target, a multispectral image is captured again. Then, a spectral image corresponding to the effective wavelength information is extracted and analyzed, and a pseudo color image is generated on the basis of a result of the analysis and the effective wavelength information and is superimposed with and displayed together with the result of the analysis.

As a result, only by imaging a target that becomes an imaging object, it is possible to implement capturing of a multispectral image in a state in which light of an appropriate wavelength corresponding to analysis of the target is applied. Further, since the analysis can be performed using a spectral image that is effective for analysis of the target that is an imaging object within the multispectral image captured in a state in which appropriate light is applied, it is possible to implement appropriate analysis of the target.

In particular, when the multispectral image is to be captured, there is no necessity for the user to set an effective wavelength for each of sites or legions in advance, and since narrow wavelength band light of the effective wavelength is applied upon the target, it is possible to capture a spectral image that is high in wavelength resolution at a wavelength effective for identification of the target.

Further, a pseudo color image is generated on the basis of a spectral image of a wavelength of light effective for a target, which is determined from a multispectral image captured using white light. This makes it possible to present a color image in which a feature of the target is emphasized to the user and to display the feature of the target in an easy-to-understand manner.

2. Second Embodiment

The foregoing description is directed to an example in which an imaging object that is a target is identifyed on the basis of a multispectral image captured by the multispectral camera 31 and an appropriate wavelength of light is specified as an effective wavelength. However, a target may be specified from a hyper multispectral image, which is generated so as to have a channel number increased on the basis of a multispectral image, to find an appropriate wavelength band of light with a higher degree of accuracy.

Figure 7:
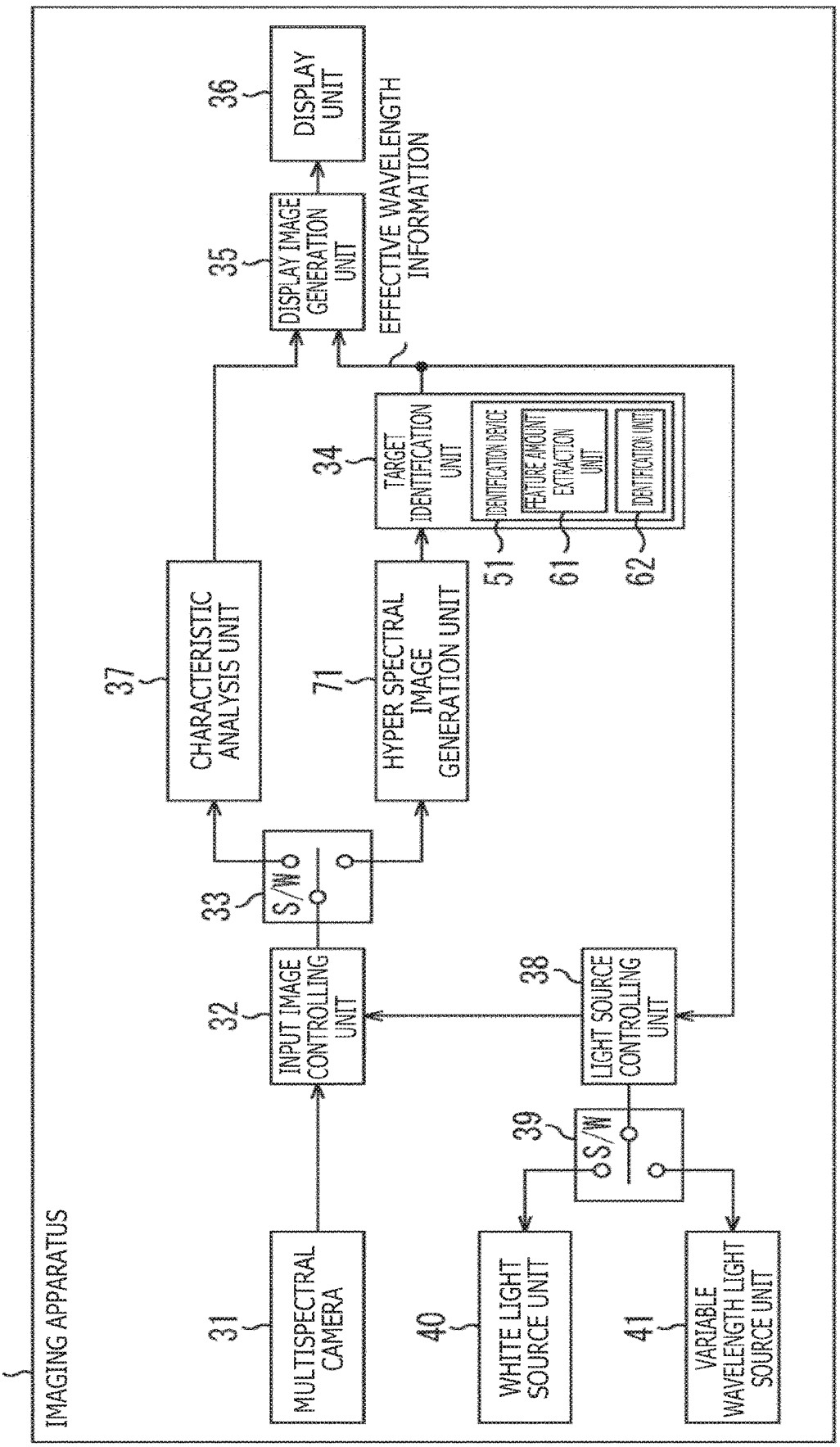
FIG. 7 is a view depicting an example of a configuration of a second embodiment of an imaging apparatus according to the present disclosure.

FIG. 7 depicts an example of a configuration of an imaging apparatus 11 that generates a hyper multispectral image having a channel number increased, on the basis of a multispectral image and specifies a target from the hyper multispectral image to find an optimum wavelength band of light with a higher degree of accuracy. It is to be noted that, in the imaging apparatus 11 of FIG. 7, components having functions identical to those of the components of the imaging apparatus 11 of FIG. 1 are denoted by identical reference signs and description of them is suitably omitted.

The imaging apparatus 11 of FIG. 7 is different from the imaging apparatus 11 of FIG. 1 in that a hyper spectral image generation unit 71 is provided between the switch 33 and the target identification unit 34.

Figure 8:
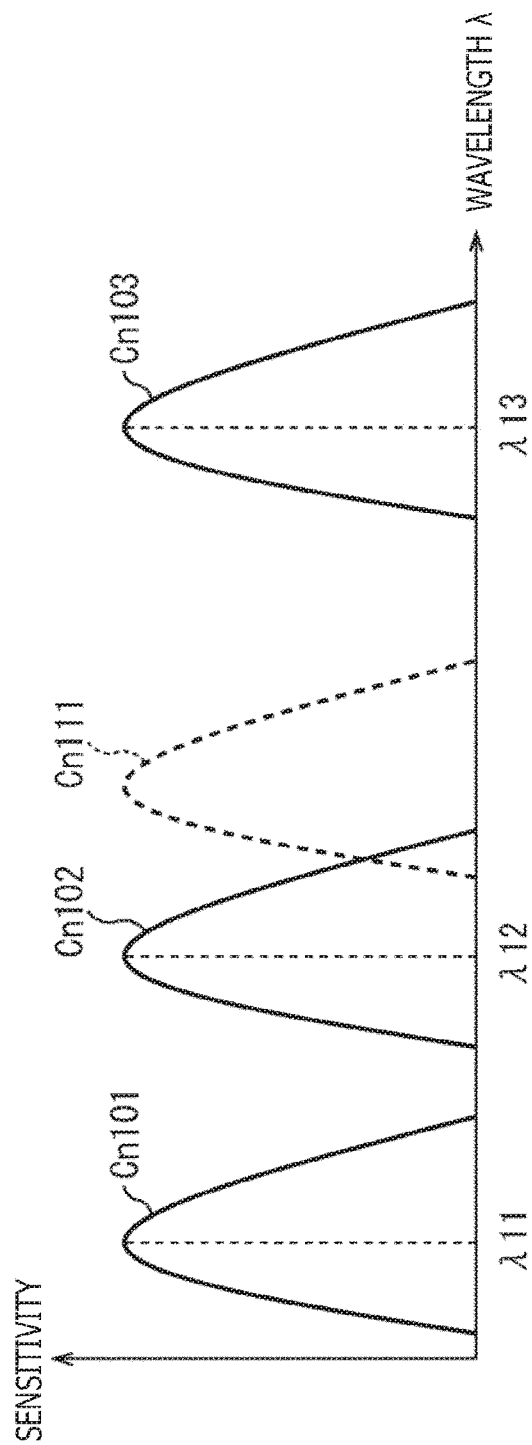
FIG. 8 is a view illustrating an example of a case in which the number of bands in a multispectral image is small.

In particular, it is assumed that, in the case where the number of wavelength bands (channel number) of the multispectral camera 31 is small and, for example, as depicted in FIG. 8, a multispectral image includes a band Cn101 having a peak at a wavelength $\lambda 11$, another band Cn102 having a peak at another wavelength $\lambda 12$, and a further band Cn103 having a peak at a further wavelength $\lambda 13$. At this time, all of the bands are not the same to an originally optimum band Cn111, and it is not considered that even the band S102 that is closest to the band Cn111 has an effective wavelength.

Figure 9:
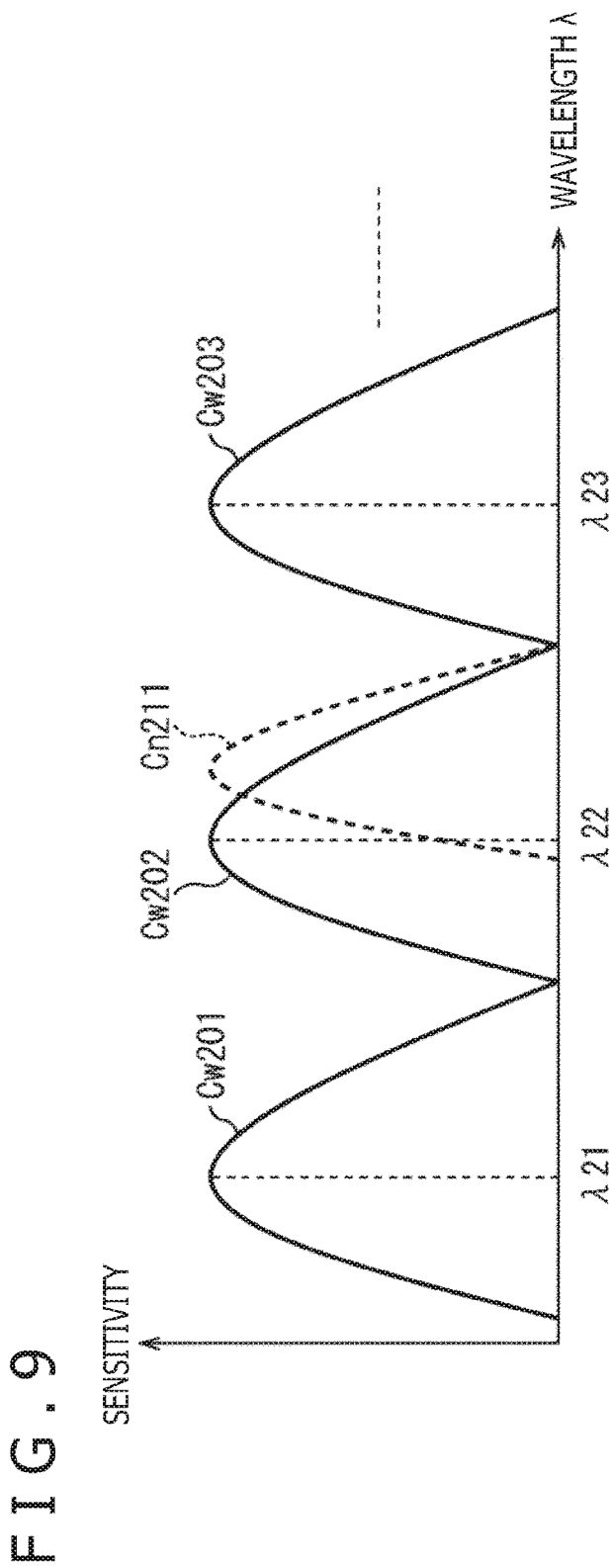
FIG. 9 is a view illustrating an example of a case in which the number of bands of a multispectral image is small.

Further, in the case where the number of wavelength bands (channel number) of the multispectral camera 31 is small and, for example, when a multispectral image includes a band Cw201 having a peak at a wavelength $\lambda 21$, another band Cw202 having a peak at another wavelength $\lambda 21$, and a further band Cw203 having a peak at a further wavelength $\lambda 23$ as depicted in FIG. 9, the bands are wider than those in the case of FIG. 8. However, all of the bands are not the same to an originally optimum band Cn211, and it is not considered that even the band Cw102 that is closest to the band Cn211 has an effective wavelength.

Thus, the hyper spectral image generation unit 71 generates a hyper spectral image of a greater number of bands (greater number of channels) on the basis of a multispectral image captured by the multispectral camera 31.

More particularly, the hyper spectral image generation unit 71 generates a hyper spectral image of a greater number of bands (greater number of channels) from the multispectral image by using, for example, the technology disclosed in Japanese Patent Laid-Open No. 2003-93336 (method of generating a spectral image of a freely-selected wavelength from an RGB image, a method in the case where the channel number is increased to four or more, and so forth). In this case, an ordinary RGB camera may be used in place of the multispectral camera 31 such that a hyper multispectral image is generated from an RGB image by the hyper spectral image generation unit 71.

As a result, even if the multispectral image generated by the multispectral camera 31 includes a smaller number of bands (smaller number of channels), effective wavelength information of high accuracy can be obtained. Further, a spectral image captured under narrow band light of the effective wavelengths can be acquired as a spectral image having a wavelength decomposition performance of a narrower band as compared to the sensitivity characteristic of the multispectral camera 31.

<Imaging Process by Imaging Apparatus of FIG. 7>

Figure 10:
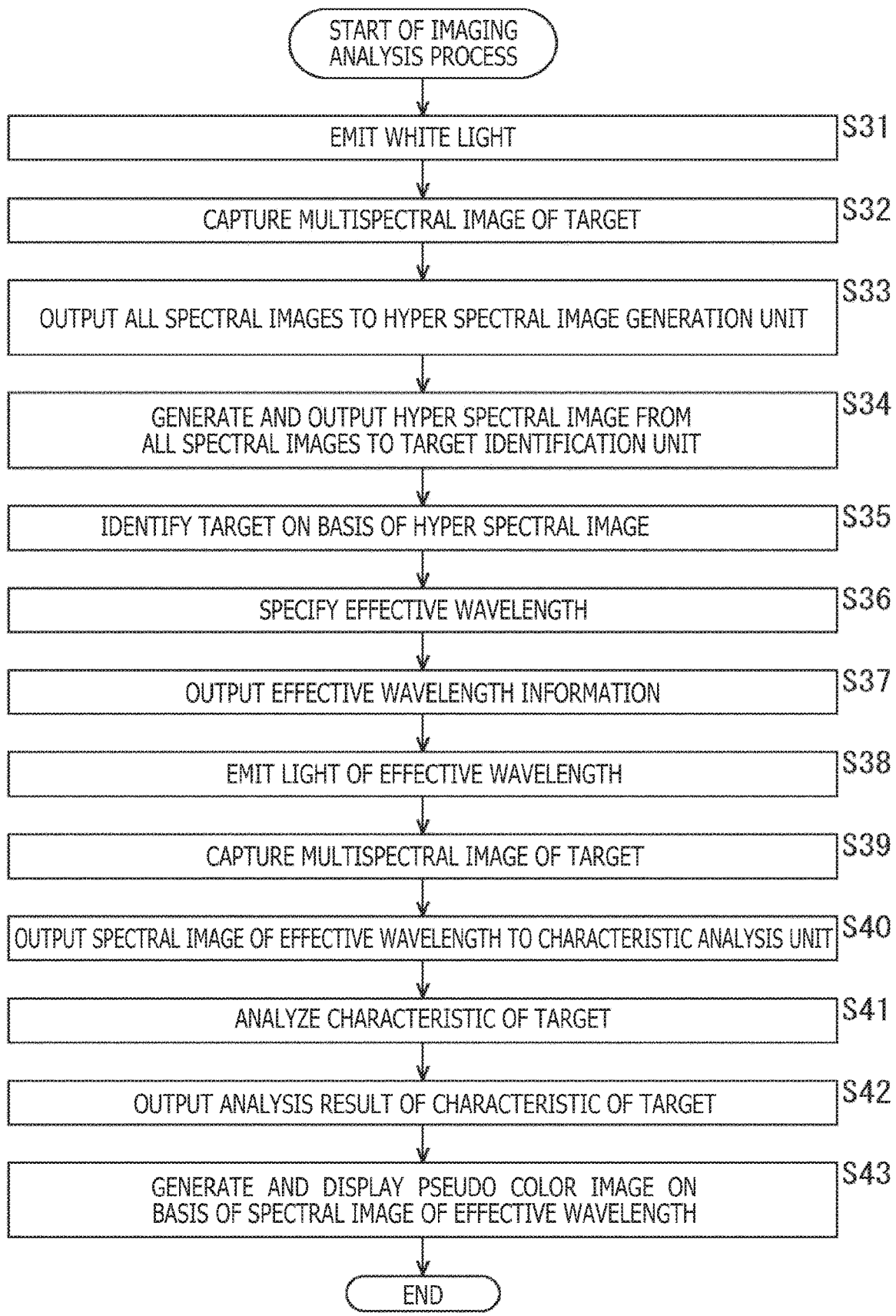
FIG. 10 is a flowchart illustrating an imaging process by the imaging apparatus of FIG. 7.

Now, an imaging process by the imaging apparatus 11 of FIG. 7 is described with reference to a flowchart of FIG. 10. It is to be noted that processes in steps S31, S32, and S37 to S43 in the flowchart of FIG. 10 are similar to the processes in steps S11, S12, and S16 to S22 in the flowchart of FIG. 7, respectively, and therefore, description of them is omitted.

In particular, if white light is applied to capture a multispectral image by the processes in steps S31 and S32, then the input image controlling unit 32 controls, in step S33, the switch 33 to establish connection to the hyper spectral image generation unit 71 and outputs all spectral images of a multispectral image captured by the multispectral camera 31 to the hyper spectral image generation unit 71.

In step S34, the hyper spectral image generation unit 71 generates a hyper spectral image from the multispectral images and outputs the hyper spectral image to the target identification unit 34.

In step S35, the target identification unit 34 identifies a target by using the identification device 51, which includes a CNN or the like, on the basis of the hyper multispectral image generated by the hyper spectral image generation unit 71.

In step S36, the target identification unit 34 specifies a wavelength of light that is effective for analysis of a target, as an effective wavelength, on the basis of a result of the target identification and the hyper spectral image.

By processes of steps subsequent to step S37, information regarding the effective wavelength is outputted as effective wavelength information and a spectral image is captured while light of an appropriate wavelength is applied upon the target. Then, the target is analyzed using the spectral image captured in the state in which light of the appropriate wavelength is applied upon the target, and a pseudo color image can be displayed.

As a result, it is possible to identify a target by using a hyper spectral image and to decide light of an appropriate wavelength on the basis of a result of the identification. Therefore, an appropriate and effective wavelength can be specified with a higher degree of accuracy, and more appropriate analysis of a target can be implemented on the basis of a spectral image where light of the effective wavelength specified with high accuracy is applied.

3. Example of Execution by Software

While the series of processes described above can be executed by hardware, it can otherwise be executed by software as well. In the case where the series of processes is executed by software, a program that is included in the software is installed from a recording medium into a computer incorporated in hardware for exclusive use, a computer for universal use that can execute various functions by installing various programs into the computer or the like.

Figure 11:
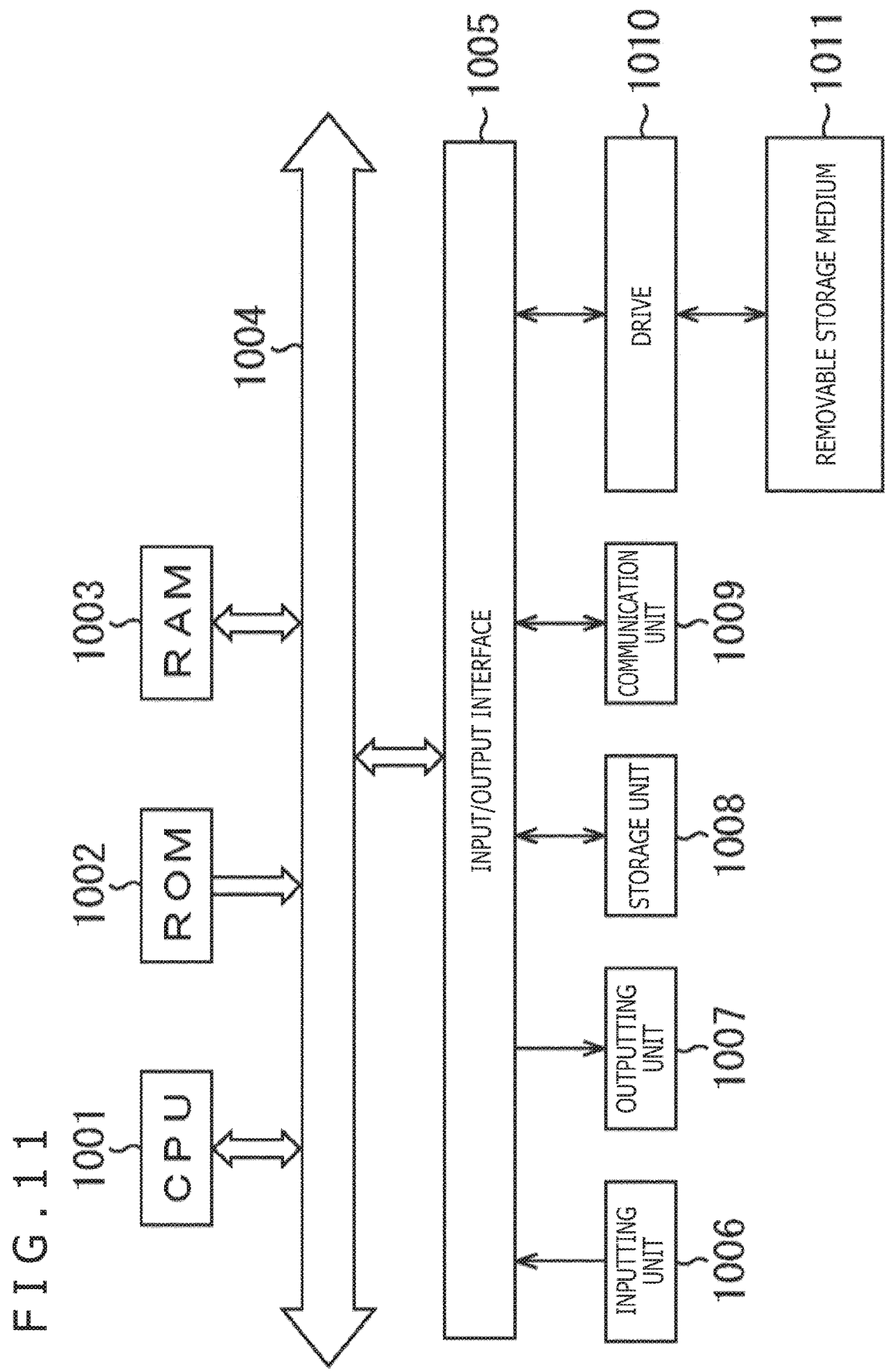
FIG. 11 is a view illustrating an example of a configuration of a general-purpose computer.

FIG. 11 depicts an example of a configuration of a computer for universal use. The personal computer has a CPU (Central Processing Unit) 1001 built therein. An input/output interface 1005 is connected to the CPU 1001 through a bus 1004. A ROM (Read Only Memory) 1002 and a RAM (Random Access Memory) 1003 are connected to the bus 1004.

To the input/output interface 1005, an inputting unit 1006 including an inputting device such as a keyboard or a mouse for allowing a user to input an operation command therethrough, an outputting unit 1007 that outputs a processing operation screen image or an image of a processing result to a display device, a storage unit 1008 including a hard disk drive for storing programs and various kinds of data therein or the like, and a communication unit 1009 that includes a LAN (Local Area Network) adapter or the like and executes a communication process through a network represented by the Internet are connected. Further, a drive 1010 for reading and writing data from and on a removable recording medium 1011 such as a magnetic disk (including a flexible disk), an optical disk (including a CD-ROM (Compact Disc-Read Only Memory) and a DVD (Digital Versatile Disc)), a magneto-optical disk (including an MD (Mini Disc)), or a semiconductor memory is connected.

The CPU 1001 executes various processes in accordance with a program stored in the ROM 1002 or a program read out from the removable recording medium 1011, such as a magnetic disk, an optical disk, a magneto-optical disk, a semiconductor memory or the like, installed in the storage unit 1008 and loaded from the storage unit 1008 in the RAM 1003. Further, in the RAM 1003, also data and so forth necessary for execution of various processes by the CPU 1001 are stored suitably.

In the computer configured in such a manner as described above, the CPU 1001 loads a program stored, for example, in the storage unit 1008 into the RAM 1003 through the input/output interface 1005 and the bus 1004 and executes the program to perform the series of processes described above.

The program to be executed by the computer (CPU 1001) can be recorded on and provided as a removable recording medium 1011 serving as, for example, a package medium. Also it is possible to provide the program through a wired or wireless transmission medium such as a local area network, the Internet, or a digital satellite broadcast.

In the computer, the program can be installed into the storage unit 1008 through the input/output interface 1005 by mounting the removable recording medium 1011 on the drive 1010. Further, the program can be received by the communication unit 1009 through a wired or wireless transmission medium and installed into the storage unit 1008. Furthermore, the program can be installed in advance in the ROM 1002 or the storage unit 1008.

It is to be noted that the program to be executed by the computer may be a program in which processes are carried out in a time series in the order as described in the present specification or a program in which processes are executed in parallel or executed at necessary timings such as when the process is called.

It is to be noted that the CPU 1001 in FIG. 11 implements the functions of the input image controlling unit 32, the target identification unit 34, characteristic analysis unit 37, the display image generation unit 35, the light source controlling unit 38, and the hyper spectral image generation unit 71 in FIGS. 1 and 7.

Further, in the present specification, the term "system" is used to signify an aggregation of plural components (devices, modules (parts) and so forth), and it does not matter whether or not all components are accommodated in the same housing. Accordingly, plural apparatuses accommodated in separate housings and connected to each other through a network are a system, and also one apparatus in which plural modules are accommodated in a single housing is a system.

It is to be noted that the embodiment of the present disclosure is not limited to the embodiments described hereinabove and allows various alterations to be made without departing from the subject matter of the present disclosure.

For example, the present disclosure can take a configuration for cloud computing by which plural apparatuses share and cooperate to process one function through a network.

Further, each of the steps described hereinabove with reference to the flowcharts can be executed by a single apparatus and can also be shared and executed by plural apparatuses.

Further, in the case where plural processes are included in one step, the plural processes included in the one step can be executed by one apparatus and can also be shared and executed by plural apparatuses.

It is to be noted that the present disclosure can also take such configurations as described below.

<1>

An imaging apparatus, including:

a white light source unit configured to apply white light on a target;

an imaging unit configured to capture a multispectral image of the target;

a target identification unit configured to specify a wavelength of light optimum for analysis of the target as an effective wavelength from the multispectral image of the target on which the white light is applied; and a variable wavelength light source unit configured to apply light having the effective wavelength on the target.

<2>

The imaging apparatus according to <1>, in which the target identification unit identifies the target from the multispectral image of the target on which the white light is applied and specifies a wavelength of light optimum for analysis of the target, as an effective wavelength, on the basis of a result of the identification.

<3>

The imaging apparatus according to <2>, in which the target identification unit uses a CNN (Convolutional Neural Network) to identify the target from the multispectral image of the target on which the white light is applied and specifies the wavelength of light optimum for analysis of the target on the basis of a result of the identification.

<4>

The imaging apparatus according to <1>, in which the imaging unit captures a multispectral image of the target on which light of the effective wavelength specified by the target identification unit is applied.

<5>

The imaging apparatus according to <4>, further including:

a characteristic analysis unit configured to analyze a characteristic of the target on the basis of a spectral image corresponding to light of the effective wavelength within the multispectral image of the target on which light of the effective wavelength specified by the target identification unit is applied.

<6>

The imaging apparatus according to <5>, in which the characteristic analysis unit uses a CNN (Convolutional Neural Network) to identify the target on the basis of a spectral image corresponding to light of the effective wavelength within the multispectral image of the target on which light of the effective wavelength specified by the target identification unit is applied, and analyzes a characteristic of the target according to a result of the identification.

<7>

The imaging apparatus according to <5>, further including:

a display image generation unit configured to allocate a spectral image that corresponds to light of the effective wavelength and emphasizes a result of the analysis performed by the characteristic analysis unit and a multispectral image other than the spectral image to R, G, and B channels to generate a pseudo color image.

<8>

The imaging apparatus according to <7>, in which the display image generation unit allocates a spectral image corresponding to light of a first effective wavelength to a first channel among the R, G, and B channels, allocates a spectral image corresponding to light of a second effective wavelength different from the first effective wavelength to a second channel among the R, G, and B channels, and allocates any other spectral image to a third channel to generate the pseudo color image.

<9>

The imaging apparatus according to <8>, in which the display image generation unit adjusts a gain of the spectral image corresponding to light of the first effective wavelength and allocates the spectral image of the adjusted gain to the first channel among the R, G, and B channels, adjusts a gain of the spectral image corresponding to light of the second effective wavelength different from the first effective wavelength and allocates the spectral image of the adjusted gain to the second channel among the R, G, and B channels, adds other spectral images to adjust the gain of a resulting image of the addition, and allocates the image of the adjusted gain to the third channel to generate the pseudo color image.

<10>

The imaging apparatus according to <7>, in which the display image generation unit allocates a spectral image corresponding to light of a first effective wavelength to a first channel among the R, G, and B channels, allocates part of spectral images other than the spectral image corresponding to light of the first effective wavelength to a second channel among the R, G, and B channels, and allocates any other than the part of the spectral images other than the spectral image corresponding to light of the first effective wavelength to a third channel to generate the pseudo color image.

<11>

The imaging apparatus according to <10>, in which the display image generation unit adjusts a gain of the spectral image corresponding to light of the first wavelength and allocates the spectral image of the adjusted gain to the first channel among the R, G, and B channels, adds part of spectral images other than the spectral image corresponding to light of the first effective wavelength, adjusts a gain of a resulting image of the addition, and allocates the image of the adjusted gain to a second channel among the R, G, and B channels, and adds any other than the part of the spectral images other than the spectral image corresponding to light of the first effective wavelength, adjusts a gain of a resulting image of the addition, and allocates the image of the adjusted gain to a third channel to generate the pseudo color image.

<12>

The imaging apparatus according to any one of <1>to <11>, further including:

a hyper spectral image generation unit configured to generate, on the basis of the multispectral image, a hyper spectral image including spectral images of bands in a number greater than that of the multispectral image, in which the target identification unit specifies, from the hyper spectral image generated on the basis of the multispectral image of the target on which the white light is applied, a wavelength of light optimum for analysis of the target, as an effective wavelength.

<13>

The imaging apparatus according to any one of <1>to <12>, in which the imaging unit captures a multispectral image of a wide wavelength band of the target.

<14>

The imaging apparatus according to any one of <1>to <13>, in which the variable wavelength light source unit emits and applies light of at least one of plural narrow wavelength bands or of a combination of the narrow wavelength bands, as light of the effective wavelength, on the target.

<15>

An imaging method, including:

a white light source process for applying white light on a target;

an imaging process for capturing a multispectral image of the target;

a target identification process for specifying a wavelength of light optimum for analysis of the target, as an effective wavelength, from the multispectral image of the target on which the white light is applied; and a variable wavelength light application process for applying light having the effective wavelength on the target.

<16>

A program for causing a computer to function as a white light source unit that applies white light on a target, an imaging unit that captures a multispectral image of the target, a target identification unit that specifies a wavelength of light optimum for analysis of the target as an effective wavelength from the multispectral image of the target on which the white light is applied, and a variable wavelength light source unit that applies light having the effective wavelength on the target.

REFERENCE SIGNS LIST

11 Imaging apparatus, 31 Multispectral camera, 32 Input image controlling unit, 33 Switch, 34 Target identification unit, 35 Display image generation unit, 36 Display unit, 37 Characteristic analysis unit, 38 Light source controlling unit, 39 Switch, 40 White light source, 41 Variable wavelength light source unit, 51 Identification device, 61 Feature amount extraction unit, 62 identification unit, 71 Hyper spectral image generation unit

The invention claimed is:

1. An imaging apparatus, comprising:
a white light source unit configured to apply white light on a target;
an imaging unit configured to capture a first multispectral image of the target based on the application of the white light on the target;
a target identification unit configured to:
identify, by use of a CNN (Convolutional Neural Network), the target from the first multispectral image;
specify, as an effective wavelength, a first wavelength of light for analysis of the target,
wherein the first wavelength of light is specified based on a first result of the identification by the target identification unit; and
a variable wavelength light source unit configured to apply light having the effective wavelength on the target.

2. The imaging apparatus according to claim 1, wherein the imaging unit is further configured to capture a second multispectral image of the target based on the application of the light of the effective wavelength specified by the target identification unit.

3. The imaging apparatus according to claim 2, further comprising a characteristic analysis unit configured to analyze a characteristic of the target based on a first spectral image corresponding to the light of the effective wavelength within the second multispectral image of the target.

4. The imaging apparatus according to claim 3, wherein the characteristic analysis unit is further configured to:
identify, by use of the CNN, the target based the first spectral image corresponding to the light of the effective wavelength within the second multispectral image of the target; and
analyze the characteristic of the target based on a second result of the identification by the characteristic analysis unit.

5. The imaging apparatus according to claim 3, further comprising a display image generation unit configured to allocate a second spectral image and a third multispectral image different from the second spectral image to R, G, and B channels to generate a pseudo color image,
wherein the second spectral image corresponds to the light of the effective wavelength and emphasizes a result of the analysis by the characteristic analysis unit.

6. The imaging apparatus according to claim 5, wherein the display image generation unit is further configured to:
allocate a third spectral image corresponding to light of a first effective wavelength to a first channel among the R, G, and B channels;
allocate a fourth spectral image corresponding to light of a second effective wavelength different from the first effective wavelength to a second channel among the R, G, and B channels;
allocate a fifth spectral image to a third channel; and
generate the pseudo color image based on the allocation of each of the third spectral image, the fourth spectral image, and the fifth spectral image.

7. The imaging apparatus according to claim 6, wherein the display image generation unit is further configured to:

adjust a gain of the third spectral image corresponding to the light of the first effective wavelength and allocate the third spectral image of the adjusted gain to the first channel among the R, G, and B channels;

adjust a gain of the fourth spectral image corresponding to the light of the second effective wavelength different from the first effective wavelength and allocate the fourth spectral image of the adjusted gain to the second channel among the R, G, and B channels;

add spectral images different from the third spectral image and the fourth spectral image;

adjust a gain of a resulting image of the addition;

allocate the resulting image of the adjusted gain to the third channel; and generate the pseudo color image based on the allocation of each of the third spectral image of the adjusted gain, the fourth spectral image of the adjusted gain, and the resulting image of the adjusted gain.

8. The imaging apparatus according to claim 5, wherein the display image generation unit is further configured to:

allocate a third spectral image corresponding to light of a first effective wavelength to a first channel among the R, G, and B channels;

allocate a first part of spectral images different from the third spectral image to a second channel among the R, G, and B channels;

allocate a second part of the spectral images to a third channel among the R, G, and B channels; and generate the pseudo color image based on the allocation of each of the third spectral image, the first part of the spectral images, and the second part of the spectral images.

9. The imaging apparatus according to claim 8, wherein the display image generation unit is further configured to:

adjust a gain of the third spectral image corresponding to the light of the first wavelength and allocate the third spectral image of the adjusted gain to the first channel among the R, G, and B channels;

add the first part of the spectral images;

adjust a gain of a first resulting image of the addition of the first part of the spectral images;

allocate the first resulting image of the adjusted gain to the second channel among the R, G, and B channels;

add the second part of the spectral images;

adjust a gain of a second resulting image of the addition of the second part of the spectral images;

allocates allocate the second resulting image of the adjusted gain to the third channel; and generate the pseudo color image based on the allocation of each of the third spectral image of the adjusted gain, the first resulting image of the adjusted gain, and the second resulting image of the adjusted gain.

10. The imaging apparatus according to claim 1, further comprising a hyper spectral image generation unit configured to generate, based on the first multispectral image, a hyper spectral image that includes spectral images having a number of bands greater than that of the first multispectral image, wherein the target identification unit is further configured to specify, from the hyper spectral image, the first wavelength of light for the analysis of the target as the effective wavelength.

11. The imaging apparatus according to claim 1, wherein the imaging unit is further configured to capture a second multispectral image of a wide wavelength band of the target.

12. The imaging apparatus according to claim 1, wherein the variable wavelength light source unit is further configured to emit and apply light of at least one of plural narrow wavelength bands or of a combination of the plural narrow wavelength bands, as the light of the effective wavelength, on the target.

13. An imaging method, comprising:

applying, by a white light source unit, white light on a target;

capturing, by an imaging unit, a multispectral image of the target based on the application of the white light on the target;

identifying, by a target identification unit, the target from the multispectral image by use of a CNN (Convolutional Neural Network);

specifying, by the target identification unit based on a result of the identification, a wavelength of light for analysis of the target as an effective wavelength; and applying, by a variable wavelength light source unit light having the effective wavelength on the target.

14. A non-transitory computer-readable medium having stored thereon computer-executable instructions, which when executed by a computer, cause the computer to execute operations, the operations comprising:

applying white light on a target;

capturing a multispectral image of the target based on the application of the white light on the target;

identifying, by use of a CNN (Convolutional Neural Network), the target from the multispectral image;

specifying, as an effective wavelength, a wavelength of light for analysis of the target,
  wherein the wavelength of light is specified based on a result of the identification; and applying light having the effective wavelength on the target.

15. An imaging apparatus, comprising:

a white light source unit configured to apply white light on a target;

an imaging unit configured to capture a multispectral image of the target based on the application of the white light on the target;

a hyper spectral image generation unit configured to generate, based on the multispectral image, a hyper spectral image that includes spectral images having a number of bands greater than that of the multispectral image;

a target identification unit configured to specify, from the hyper spectral image, a wavelength of light for analysis of the target as an effective wavelength; and a variable wavelength light source unit configured to apply light having the effective wavelength on the target.

* * * * *